(12) United States Patent
Crutchfield et al.

(10) Patent No.: US 12,707,980 B2
(45) Date of Patent: Aug. 11, 2026

(54) INTEGRATED CIRCUIT PACKAGE AND MEDICAL DEVICE INCLUDING SAME

(71) Applicant: Medtronic, Inc., Minneapolis, MN (US)

(72) Inventors: Randolph E. Crutchfield, Scottsdale, AZ (US); Jeff M. Wheeler, Gilbert, AZ (US)

(73) Assignee: Medtronic, Inc., Minneapolis, MN (US)

( * ) Notice: Subject to any disclaimer, the term of this patent is extended or adjusted under 35 U.S.C. 154(b) by 795 days.

(21) Appl. No.: 17/846,601

(22) Filed: Jun. 22, 2022

(65) Prior Publication Data

US 2023/0420383 A1 Dec. 28, 2023

(51) Int. Cl.
*H01L 23/552* (2006.01)
*A61N 1/05* (2006.01)
(Continued)

(52) U.S. Cl.
CPC .......... *H10W 42/20* (2026.01); *A61N 1/0504* (2013.01); *A61N 1/375* (2013.01);
(Continued)

(58) Field of Classification Search
CPC ............. H01L 23/552; H01L 21/76829; H01L 21/76895; H01L 23/528; H01L 23/3171; H01L 23/5222–5225; H01L 23/556; A61N 1/0504; A61N 1/509; A61N 1/0531; A61N 1/0534; A61N 1/0541; A61N 1/36038;
(Continued)

(56) References Cited

U.S. PATENT DOCUMENTS 8,178,953 B2 5/2012 Barth et al.
8,421,158 B2 * 4/2013 Lin ........................ H01L 27/04 257/E27.024
(Continued)

OTHER PUBLICATIONS

International Searching Authority, Written Opinion of the International Searching Authority, International application No. PCT/IB2023/056268, Dec. 28, 2023, all pages. (Year: 2023).*
(Continued)

*Primary Examiner* — Victoria K. Hall
(74) *Attorney, Agent, or Firm* — Mueting Raasch Group

(57) ABSTRACT

Various embodiments of an integrated circuit package are disclosed. The package includes an integrated circuit having an integrated circuit contact disposed on a first major surface of the integrated circuit; a first passivation layer disposed on the first major surface of the integrated circuit and over the integrated circuit contact; and a redistribution layer disposed on the first passivation layer. The redistribution layer includes a conductive trace and a shield region that define a plane of the redistribution layer. The package further includes a second passivation layer disposed on the redistribution layer, and a patterned conductive layer disposed on the second passivation layer and including a conductive trace. A portion of the shield region of the redistribution layer is disposed between the conductive trace of the patterned conductive layer and the integrated circuit along an axis that is substantially orthogonal to the first major surface of the integrated circuit.

20 Claims, 5 Drawing Sheets

(51) Int. Cl.

| | |
|---|---|
| ***A61N 1/375*** | (2006.01) |
| ***H01L 21/768*** | (2006.01) |
| ***H01L 23/522*** | (2006.01) |
| ***H01L 23/528*** | (2006.01) |
| ***H10W 20/00*** | (2026.01) |
| ***H10W 20/40*** | (2026.01) |
| ***H10W 20/41*** | (2026.01) |
| ***H10W 20/43*** | (2026.01) |
| ***H10W 42/20*** | (2026.01) |
| ***H10W 42/25*** | (2026.01) |
| *A61N 1/36* | (2006.01) |
| *A61N 1/362* | (2006.01) |
| *A61N 1/39* | (2006.01) |
| *H10W 70/654* | (2026.01) |
| *H10W 70/69* | (2026.01) |

(52) U.S. Cl.
CPC ..... *H10W 20/0698* (2026.01); *H10W 20/074* (2026.01); *H10W 20/423* (2026.01); *H10W 20/43* (2026.01); *H10W 20/495* (2026.01); *H10W 42/25* (2026.01); *A61N 1/0509* (2013.01); *A61N 1/0531* (2013.01); *A61N 1/0534* (2013.01); *A61N 1/0541* (2013.01); *A61N 1/36038* (2017.08); *A61N 1/36053* (2013.01); *A61N 1/36062* (2017.08); *A61N 1/362* (2013.01); *A61N 1/3756* (2013.01); *A61N 1/3956* (2013.01); *H10W 70/654* (2026.01); *H10W 70/69* (2026.01)

(58) Field of Classification Search
CPC ............ A61N 1/36053; A61N 1/36062; A61N 1/362; A61N 1/3756; A61N 1/3956; A61N 1/375; H10W 20/423; H10W 42/20–287; H10W 74/137
See application file for complete search history.

(56) References Cited

U.S. PATENT DOCUMENTS

| | | | | |
|---|---|---|---|---|
| 8,588,914 | B2 * | 11/2013 | Rooney | A61N 1/37518 607/36 |
| 9,589,909 | B1 | 3/2017 | Yap et al. | |
| 9,836,095 | B1 * | 12/2017 | Lim | H01L 24/33 |
| 11,213,690 | B2 | 1/2022 | Boone et al. | |
| 11,270,953 | B2 * | 3/2022 | Chuang | H01L 23/49816 |
| 2004/0222511 | A1 | 11/2004 | Zhang | |
| 2004/0245580 | A1 * | 12/2004 | Lin | H10D 84/00 257/536 |
| 2005/0040500 | A1 * | 2/2005 | Henmi | H01L 23/5225 257/659 |
| 2007/0073353 | A1 * | 3/2007 | Rooney | A61N 1/0531 607/36 |
| 2010/0140760 | A1 * | 6/2010 | Tam | H01L 24/05 257/E23.115 |
| 2015/0102472 | A1 * | 4/2015 | Tsai | H01L 23/552 257/659 |
| 2020/0075503 | A1 * | 3/2020 | Chuang | H01L 25/165 |
| 2021/0343656 | A1 * | 11/2021 | Kwon | H10W 42/121 |

OTHER PUBLICATIONS

International Searching Authority, International Search Report, International application No. PCT/IB2023/056268, Dec. 28, 2023, all pages. (Year: 2023).*

* cited by examiner

INTEGRATED CIRCUIT PACKAGE AND MEDICAL DEVICE INCLUDING SAME

TECHNICAL FIELD

This disclosure generally relates to an integrated circuit package and more particularly to a medical device that includes such integrated circuit package.

BACKGROUND

Medical devices such as implantable medical devices (IMDs) can include a variety of components that deliver therapy (such as electrical stimulation or drugs) to a patient, monitor a physiological parameter of a patient, or both. IMDs typically include one or more functional components encased in a housing that can be implanted in a body of the patient. For example, the housing can be implanted in a pocket created in a torso of the patient. The housing can include various circuitry and components such as integrated circuit packages that can be utilized to deliver energy for therapy to a patient, monitor a physiological parameter of a patient, or control the functionality of the medical device.

Such integrated circuit packages can include one or more redistribution layers that can be electrically connected to an integrated circuit of the package and help spread electrical contact points of the integrated circuit to one or more contact pads elsewhere in the package such that additional integrated circuits and devices can be electrically connected to the original integrated circuit.

SUMMARY

The techniques of this disclosure generally relate to an integrated circuit package and a medical device that includes such package. The package can include an integrated circuit and a redistribution layer that includes one or more conductive traces and one or more shield regions. A patterned conductive layer can be disposed such that the redistribution layer is between the patterned conductive layer and the integrated circuit. A portion of at least one of the shield regions of the redistribution layer can be disposed between one or more conductive traces of the patterned conductive layer and the integrated circuit. In one or more embodiments, such shield region can be configured to reduce parasitic capacitance between the integrated circuit and the patterned conductive layer. Further, in one or more embodiments, such shield region can be configured to dissipate ionizing radiation that is incident upon the shield region, thereby potentially preventing this ionizing radiation from being incident upon the integrated circuit.

This disclosure includes without limitation the following clauses:

Clause 1: An integrated circuit package that includes an integrated circuit having a first major surface, a second major surface, and an integrated circuit contact disposed on the first major surface; a first passivation layer disposed on the first major surface of the integrated circuit and over the integrated circuit contact; and a redistribution layer disposed on the first passivation layer, where the redistribution layer includes a conductive trace and a shield region, where the conductive trace and the shield region define a plane of the redistribution layer. The package further includes a second passivation layer disposed on the redistribution layer, and a patterned conductive layer disposed on the second passivation layer and including a conductive trace, where a portion of the shield region of the redistribution layer is disposed between the conductive trace of the patterned conductive layer and the integrated circuit along an axis that is substantially orthogonal to the first major surface of the integrated circuit.

Clause 2: The package of Clause 1, where the shield region of the redistribution layer is configured to reduce parasitic capacitance between the integrated circuit and the patterned conductive layer.

Clause 3: The package of Clause 1, where the shield region of the redistribution layer is configured to dissipate ionizing radiation incident upon the shield region.

Clause 4: The package of Clause 1, where the shield region of the redistribution layer includes a mesh having a plurality of openings.

Clause 5: The package of Clause 1, where the integrated circuit includes a substrate and an active area disposed on the substrate, where the active area is electrically connected to the integrated circuit contact.

Clause 6: The package of Clause 5, where the integrated circuit contact is electrically connected to the redistribution layer by a conductive via that extends through the first passivation layer.

Clause 7: The package of Clause 1, where the shield region is grounded.

Claus 8: The package of Clause 1, where the patterned conductive layer further includes a conductive pad electrically connected to the redistribution layer and the integrated circuit.

Clause 9: A method that includes disposing a first passivation layer on a first major surface of an integrated circuit, where the integrated circuit includes an integrated circuit contact that is disposed on the first major surface, where the integrated circuit further includes a second major surface; disposing a redistribution layer on the first passivation layer; and patterning the redistribution layer to form a conductive trace and a shield region, where the conductive trace and the shield region define a plane of the redistribution layer. The method further includes electrically connecting the conductive trace of the redistribution layer to the integrated circuit contact through the first passivation layer; disposing a second passivation layer on the redistribution layer; and disposing a patterned conductive layer on the second passivation layer, where the patterned conductive layer includes a conductive trace, and where a portion of the shield region of the redistribution layer is disposed between the conductive trace of the patterned conductive layer and the integrated circuit along an axis that is substantially orthogonal to the first major surface of the integrated circuit.

Clause 10: The method of Clause 9, where the shield region of the redistribution layer includes a mesh having a plurality of openings disposed through the shield region.

Clause 11: The method of Clause 9, further including disposing a via through the first passivation layer that electrically connects the integrated circuit contact to the conductive trace of the redistribution layer.

Clause 12: The method of Clause 9, further including grounding the shield region of the redistribution layer.

Clause 13: The method of Clause 9, where disposing the patterned conductive layer includes disposing a conductive layer on the second passivation layer, and patterning the conductive layer to form the conductive trace and a conductive pad.

Clause 14: The method of Clause 13, further including disposing a conductive via through the second passivation layer that electrically connects the conductive pad of the patterned conductive layer to the conductive trace of the redistribution layer.

Clause 15: A medical device including a housing and circuitry disposed within the housing, where the circuitry includes an integrated circuit package. The package includes an integrated circuit including a first major surface, a second major surface, and an integrated circuit contact disposed on the first major surface; a first passivation layer disposed on the first major surface of the integrated circuit and over the integrated circuit contact; and a redistribution layer disposed on the first passivation layer, where the redistribution layer includes a conductive trace and a shield region, and where the conductive trace and the shield region define a plane of the redistribution layer. The package further includes a second passivation layer disposed on the redistribution layer, and a patterned conductive layer disposed on the second passivation layer and including a conductive trace. A portion of the shield region of the redistribution layer is disposed between the conductive trace of the patterned conductive layer and the integrated circuit along an axis that is substantially orthogonal to the first major surface of the integrated circuit.

Clause 16: The device of Clause 15, where the shield region of the redistribution layer is grounded to the housing.

Clause 17: The device of Clause 15, further including an electrode disposed on an outer surface of the housing, where the integrated circuit package is electrically connected to the electrode.

Clause 18: The device of Clause 15, where the shield region of the redistribution layer is configured to reduce parasitic capacitance between the integrated circuit and the patterned conductive layer.

Clause 19: The device of Clause 15, where the shield region of the redistribution layer includes a mesh that has a plurality of openings disposed through the shield region.

Clause 20: The device of Clause 15, where the integrated circuit includes a substrate and an active area disposed on the substrate, where the active area is electrically connected to the integrated circuit contact.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
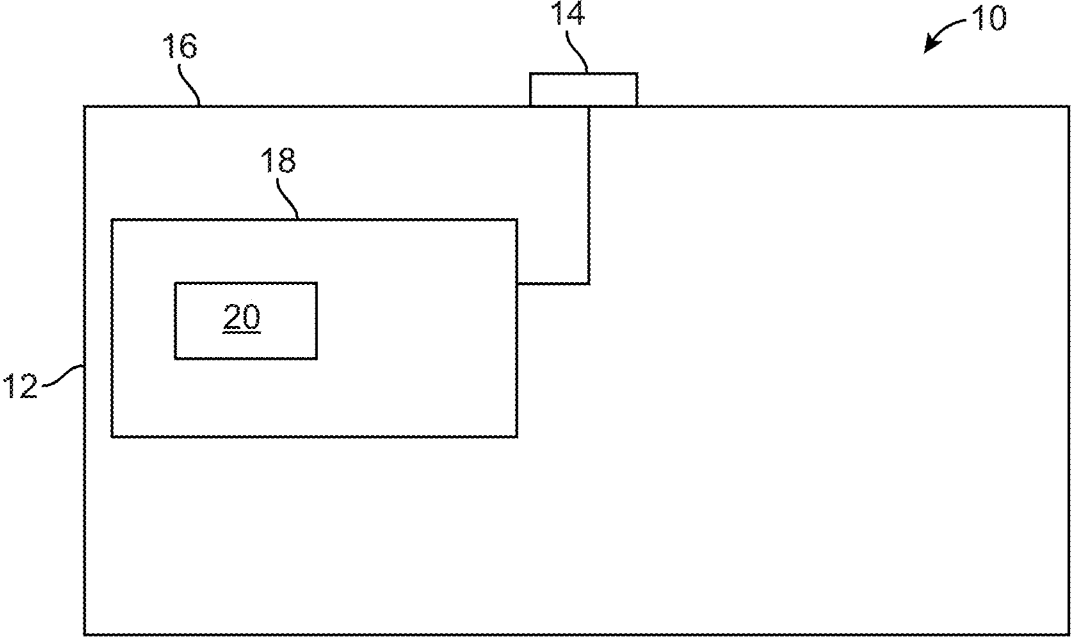
FIG. 1 is a schematic view of one embodiment of a medical device that includes an integrated circuit package.

The techniques of this disclosure generally relate to an integrated circuit package and a medical device that includes such package. The package can include an integrated circuit and a redistribution layer that includes one or more conductive traces and one or more shield regions. A patterned conductive layer can be disposed such that the redistribution layer is between the patterned conductive layer and the integrated circuit. A portion of at least one of the shield regions of the redistribution layer can be disposed between one or more conductive traces of the patterned conductive layer and the integrated circuit. In one or more embodiments, such shield region can be configured to reduce parasitic capacitance between the integrated circuit and the patterned conductive layer. Further, in one or more embodiments, such shield region can be configured to dissipate ionizing radiation that is incident upon the shield region, thereby potentially preventing this ionizing radiation from being incident upon the integrated circuit.

Advanced integrated circuit packaging technology can allow packages to be stacked vertically in a direction generally orthogonal to a plane of the integrated circuit, thereby creating three-dimensional packages that can aid miniaturization of electronic modules that include these packages. This vertical stacking can, however, create signal integrity challenges as the multiple layers of metal interconnects of the package can form parasitic capacitances within the package. As medical devices continue to be miniaturized, it can become more challenging to provide the necessary electrical signal integrity for proper operation of a device that includes these vertically-stacked packages.

One or more embodiments of integrated circuit packages described herein can provide various advantages over known integrated circuit packages. For example, one or more embodiments of integrated circuit packages can improve signal integrity of the circuits disposed within the package. Such improvement can be provided by reducing parasitic capacitance that can be formed between layers within the package using one or more shield regions disposed between two or more of the layers. Such shield regions can be a part of a redistribution layer that also functions to distribute electrical connections from an integrated circuit to other circuitry or devices disposed within the package or external to the package. For example, a redistribution layer can include one or more conductive traces and one or more shield regions, where the conductive traces and shield regions define a plane of the redistribution layer. Such shield regions can interrupt the formation of parasitic capacitances between conductive layers of the package, thereby improving signal integrity of the package.

Further, some of the materials used in integrated circuit packaging can emit ionizing radiation (e.g., alpha particles). Such radiation can cause single event upsets (SEU). This ionizing radiation can be mitigated by the one or more shield regions of the redistribution layer, which can isolate sensitive circuitry from the radiation.

The various embodiments of integrated circuit packages described herein can be utilized with any suitable device. In one or more embodiments, the integrated circuit packages of the disclosure can be utilized with a medical device. For example, FIG. 1 is a schematic view of one embodiment of a medical device 10. The device 10 includes a housing 12 and circuitry 18 disposed within the housing. The device 10 can also include an electrode 14 disposed on or at least partially within an outer surface 16 of the housing 12. The circuitry 18 is electrically connected to the electrode 14 using any suitable technique. The circuitry 18 includes an integrated circuit package 20 as is further described herein.

The device 10 can include any suitable medical device. In one or more embodiments, the device 10 can include an implantable medical device such as a cochlear implant; a sensing or monitoring device; a signal generator such as a cardiac pacemaker or defibrillator, a neurostimulator (e.g., a spinal cord stimulator, a brain or deep brain stimulator, a peripheral nerve stimulator, a vagal nerve stimulator, an occipital nerve stimulator, a subcutaneous stimulator, etc.), or a gastric stimulator; or the like. In one or more embodiments, the device 10 can include a leadless pacemaker.

The housing 12 of the device 10 can take any suitable shape and have any suitable dimensions. Further, the housing 12 can include any suitable material or materials, e.g., polymeric materials or inorganic materials such as metallic or ceramic materials. Suitable materials for the housing 12 can include at least one of titanium (e.g., any suitable grade such as grade 5 titanium), stainless steel, polymer, ceramic, glass, or combinations thereof such as laminates, composites, or miscible blends or mixtures. Suitable polymeric materials for the housing 12 can include at least one of epoxy, polyurethane, silicone, polyolefin, acrylic polymer, polyester, polyetheletherketone, polysulfone, polymethylene oxide, or polyvinyl material, or combinations thereof.

The housing 12 can be a unitary housing. In one or more embodiments, the housing 12 can include two or more portions that are connected using any suitable technique, e.g., welding, mechanically fastening, adhering, thermal bonding, diffusion bonding, laser-assisted diffusion bonding, solvent bonding, etc. Further, the housing 12 can be formed using any suitable technique, e.g., molding, thermoforming, laminating, over-molding, casting, insert molding, etc.

Disposed on the outer surface 16 of the housing 12 is the electrode 14, which can be disposed on or in any suitable portion of the device 10. The electrode 14 can be electrically connected to the circuitry 18 using any suitable technique. The electrode 14 can include any suitable electrode that is configured to direct electrical energy from the circuitry 18 to tissue of a patient. Further, the electrode 14 can include any suitable electrode that is configured to receive electrical energy from tissue, e.g., one or more electrical signals from the heart. Although depicted as included a single electrode 14, the device 10 can include any suitable number of electrodes disposed on or at least partially within any suitable portions of the device.

The circuitry 18, which is disposed within the housing 12 of the device 10, can include any suitable discrete and/or integrated electronic circuit components that implement analog and/or digital circuits capable of producing the functions attributed to the device 10. In one or more embodiments, the circuitry 18 can also include components for sensing other physiological parameters, such as acceleration, pressure, sound, and/or impedance. The circuitry 18 can further include any suitable electronic component, e.g., at least one of a capacitor, transistor, integrated circuit, including controller or multiplexer, sensor, accelerometer, inductive charging coil, optical components such as emitters and detectors, etc. The device 10 can include any suitable number of electronic components of circuitry 18. Further, the device 10 can include one or more additional electronic components or elements disposed on the outer surface 16 of the housing 12 that are electrically connected to the circuitry within the housing using any suitable technique.

The circuitry 18 can also include a battery or other power source. In one or more embodiments, the battery is a rechargeable battery that can be recharged using any suitable technique using a charging coil (not shown) that is electrically connected to the battery.

Figure 2:
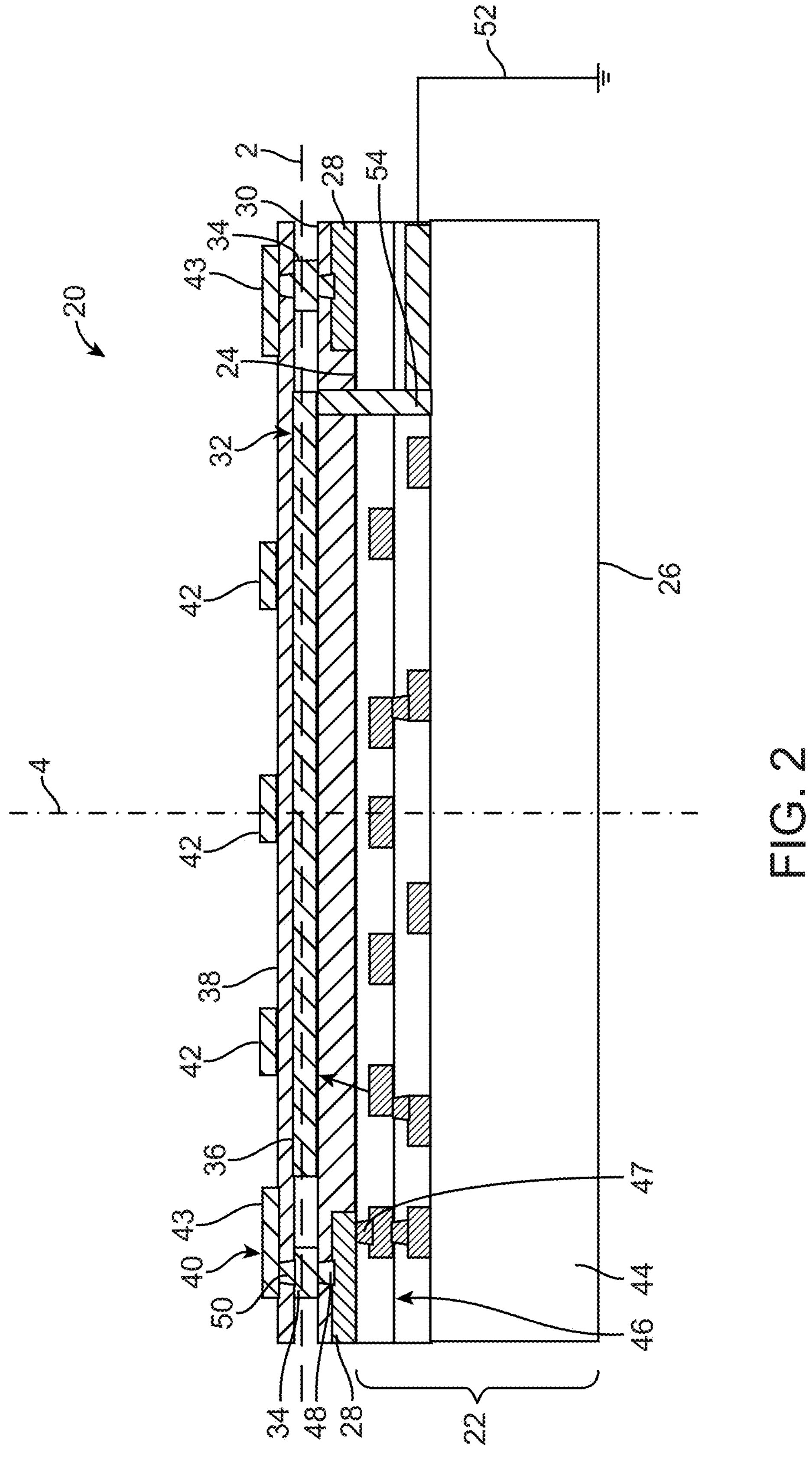
FIG. 2 is schematic cross-section view of the integrated circuit package of FIG. 1.
Figure 3:
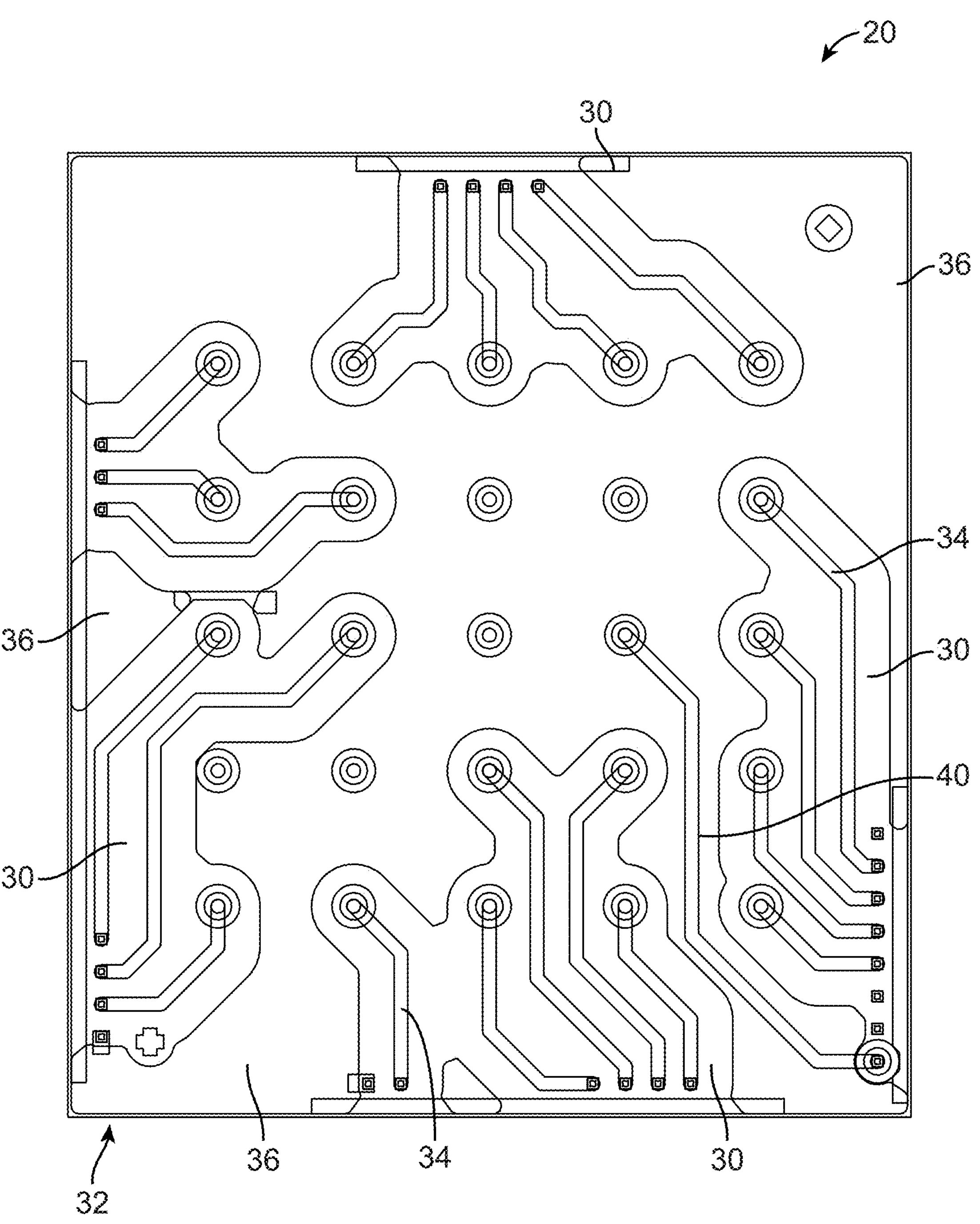
FIG. 3 is a schematic top plan view of the integrated circuit package of FIG. 1 with a second passivation layer made transparent for clarity.

As mentioned herein, circuitry 18 includes one or more integrated circuit packages 20. The device 10 can include any suitable integrated circuit package 20. As shown in FIGS. 2-3, the package 20 includes an integrated circuit 22, a patterned conductive layer and a redistribution layer 32 disposed between the integrated circuit and the patterned conductive layer. The integrated circuit 22 includes a first major surface 24, a second major surface 26, and one or more integrated circuit contacts 28 disposed on the first major surface of the circuit. Although not shown, the integrated circuit package 20 can be packaged in any suitable material or materials, e.g., silicon, sapphire, glass, or polyimide or other polymers. Further, the integrated circuit package 20 can take any suitable shape and have any suitable dimensions.

The package 20 can also include a first passivation layer 30 disposed on the first major surface 24 of the integrated circuit 22 and over the integrated circuit contacts 28, and the redistribution layer 32 disposed on the first passivation layer. The redistribution layer 32 includes one or more conductive traces 34 and one or more shield regions 36. Further, the conductive trace 34 and the shield region 36 define a plane 2 of the redistribution layer 32. The package 20 further includes a second passivation layer 38 disposed on the redistribution layer 32, and the patterned conductive layer 40 disposed on the second passivation layer and including one or more conductive traces 42. A portion of the shield region 36 of the redistribution layer 32 is disposed between one or more of the conductive traces 42 of the patterned conductive layer 40 and the integrated circuit 22 along an axis 4 that is substantially orthogonal to the first major surface 24 of the integrated circuit 22.

The integrated circuit 22 can include any suitable circuit or circuits. As shown in FIG. 2, the integrated circuit 22 includes a substrate 44 and an active area 46 disposed on the substrate. The active area 46 can be electrically connected to the integrated circuit contacts 28 using any suitable technique. In one or more embodiments, one or more vias 47 can extend between the active area 46 and the integrated circuit contacts 28.

The substrate 44 can include any suitable material or materials, e.g., inorganic materials such as metallic or ceramic materials, polymeric materials, or combinations thereof. In one or more embodiments, the substrate 44 can be a nonconductive substrate that provides electrical isolation between various conductors, vias, dies, etc. In one or more embodiments, the substrate 44 can include a semiconductive material or materials. In one or more embodiments, the substrate 44 can include at least one of silicon, germanium, gallium arsenide, silicon carbide, gallium nitride, gallium phosphide, cadmium sulfide, lead sulfide, or polymer semiconductors.

The active area 46 of the integrated circuit 22 can include any suitable electronic elements or devices, e.g., at least one of an active or a passive device. In one or more embodiments, the active area 46 can include at least one of a field effect transistor (FET), metal oxide semiconductor (MOS), MOSFET, insulated gate bipolar junction transistor (IGBT), thyristor, bipolar transistor, diode, MOS-controlled thyristor, resistor, capacitor, inductor, sensor-mixed signal application-specific integrated circuit (ASIC), digital circuit, or analog circuit. The various devices of the active area 46 can be electrically connected using any suitable technique.

Electrically connected to the active area 46 are the one or more integrated circuit contacts 28. Although depicted as being disposed on the first major surface 24 of the integrated circuit 22, the integrated circuit contacts 28 can be disposed on or within any suitable portion or portions of the integrated circuit. Further, the integrated circuit 22 can include any suitable number of contacts 28. The contacts 28 can take any suitable shape and have any suitable dimensions. Further, the contacts 28 can include any suitable conductive material or materials and be formed using any suitable technique. The contacts 28 can provide one or more electrical connections between the devices of the integrated circuit 22 and one or more devices that are external to the integrated circuit.

Disposed on the first major surface 24 of the integrated circuit 22 is the first passivation layer 30, which can include any suitable nonconductive material, e.g., polyimide or other polymers, silicon oxide, etc. Although depicted as a single layer, the first passivation layer 30 can include any suitable number of sublayers of nonconductive material. Further, the first passivation layer 30 can take any suitable shape and have any suitable dimensions. In one or more embodiments, the first passivation layer 30 is configured to electrically isolate the integrated circuit 22 from the redistribution layer 32 except for electrical connections between the integrated circuit contacts 28 and the redistribution layer. The first passivation layer 30 can be disposed on the integrated circuit 22 and over the integrated circuit contacts 28 using any suitable technique, e.g., spin coating. In one or more embodiments, the first passivation layer 30 can be disposed on and in contact with at least one of the integrated circuit 22 or the integrated circuit contacts 28. In one or more embodiments, one or more additional layers can be disposed between the integrated circuit 22 and the first passivation layer 30.

The redistribution layer 32 can be disposed on or at least partially within any portion or portions of the first passivation layer 30. Although depicted as a single layer, the redistribution layer 32 can include any suitable number of sublayers. The redistribution layer 32 includes one or more conductive traces 34 and one or more shield regions 36. The conductive traces 34 and the shield regions 36 can define the plane 2 of the redistribution layer 32. Further, the redistribution layer 32 can take any suitable shape and have any suitable dimensions. The redistribution layer 32 can include any suitable conductive material. In general, the redistribution layer 32 is configured to reroute electrical connections between the integrated circuit 22 and other desired locations within the package 20 or external to the package.

The redistribution layer 32 can be patterned using any suitable technique to provide the conductive traces 34 and the shield regions 36. Such patterning can provide any suitable number of conductive traces 34 that can take any suitable shape in a plane parallel to the first major surface 24 of the integrated circuit 22 (i.e., the plane of FIG. 3). The conductive traces 34 can be electrically connected to the integrated circuit 22 using any suitable technique. In one or more embodiments, one or more vias 48 can be disposed in the first passivation layer 30 such that they extend between the integrated circuit contacts 28 and one or more of the conductive traces 34 of the redistribution layer 32. Any suitable technique can be utilized to form the conductive vias 48. Further, one or more of the conductive traces 34 of the redistribution layer 32 can be electrically connected to the patterned conductive layer 40 using any suitable technique. In one or more embodiments, one or more vias 50 can be disposed in the second passivation layer 38 such that they extend between one or more of the conductive traces 34 and the patterned conductive layer Any suitable technique can be utilized to form the conductive vias 50.

The redistribution layer 32 can also include any suitable number of shield regions 36. Such shield regions 36 can take any suitable shape and have any suitable dimensions. Further, one or more portions of the shield region 36 can be disposed between one or more conductive traces 42 of the patterned conductive layer 40 and the integrated circuit 22 along the axis 4 that is substantially orthogonal to the first major surface 24 of the integrated circuit. As used herein, the term "substantially orthogonal" means that the axis 4 is disposed relative to the first major surface 24 of the integrated circuit 22 such that an angle formed between the axis and the first major surface is greater than 85 degrees and no greater than 95 degrees. When positioned between the conductive traces 42 and the integrated circuit 22, the shield region 36 can be configured to reduce parasitic capacitance between the integrated circuit and the patterned conductive layer 40 using any suitable technique. In one or more embodiments, the shield region 36 can provide a protective electrical barrier between aggressor and victim signals within at least one of the integrated circuit 22 or the redistribution layer 32. Interference between electrical signals is known as "crosstalk," which can be caused by capacitive coupling between conductors, where switching on one signal, called the aggressor, can influence another signal, called the victim. This may in some cases cause a change in value of the victim signal, or it could delay a signal transition that affects timing. Changes in the value of the victim signal can be classified as a signal integrity issue. Further, the shield region 36 of the redistribution layer 32 can be configured to dissipate ionizing radiation incident upon the shield region using any suitable technique. In general, the shield region 36 can have an area in a plane parallel to the first major surface of the integrated circuit 22 that is greater than what is needed for electrical performance yet provides shielding of the integrated circuit 22 from such ionizing radiation.

In one or more embodiments, the shield region 36 can include a mesh that includes a plurality of openings. Any suitable mesh can be selected depending upon various factors such as one or more frequencies of electric signals that may be incident upon the mesh from the integrated circuit 22 or other components or devices of the package or external to the package.

Figure 4:
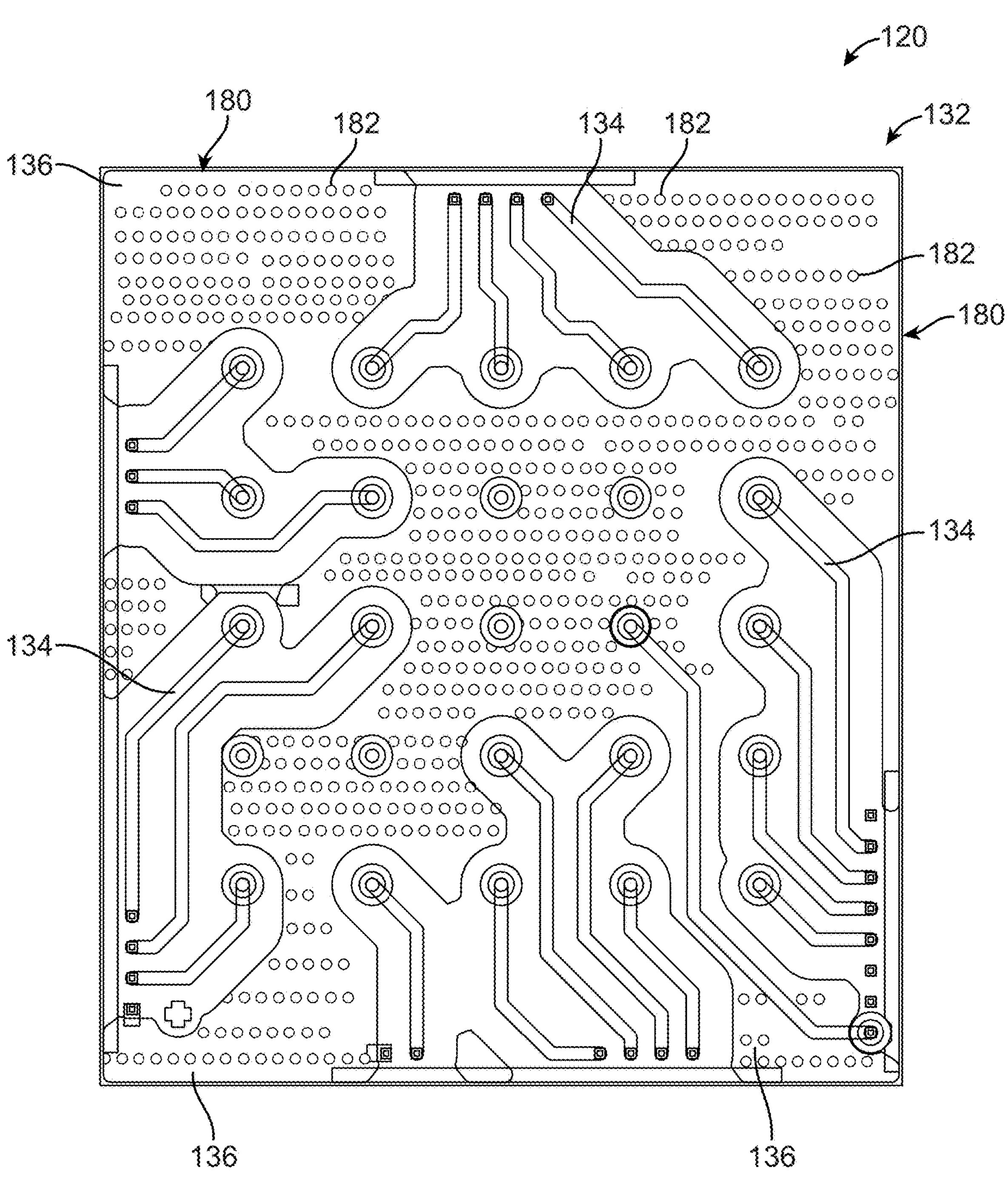
FIG. 4 is a schematic top plan view of another embodiment of an integrated circuit package.

For example, FIG. 4 is a schematic plan view of another embodiment of an integrated circuit package 120 that includes a redistribution layer 132. All design considerations and possibilities described herein regarding the integrated circuit package 20 of FIGS. 1-3 apply equally to the integrated circuit package 120 of FIG. 4. The package 120 includes a redistribution layer 132 that has one or more conductive traces 134 and one or more shield regions 136.

One difference between redistribution layer 132 of FIG. 4 and redistribution layer 32 of the package 20 of FIGS. 1-3 is that the shield regions 136 are disposed as a mesh 180 that includes a plurality of openings 182. The openings 182 of the mesh 180 can take any suitable shape and have any suitable dimensions. Further, the mesh 180 can be formed using any suitable technique. The redistribution layer 132 can be utilized with any suitable device or integrated circuit package, e.g., integrated circuit package 20 of FIGS. 1-3. In one or more embodiments, mesh 180 can enhance adhesion between the various layers that are disposed on the redistribution layer 132.

Returning to FIGS. 1-3, the shield region 36 can be connected to ground 52 using any suitable technique. In one or more embodiments, the shield region 36 can be connected to ground 52 utilizing one or more vias 54 disposed through any suitable portions of the package, e.g., through at least one of the first passivation layer 30 or the integrated circuit 22. In one or more embodiments, the shield region 36 can be electrically connected to a ground terminal of the integrated circuit 22. In one or more embodiments, the shield region 36 can be electrically connected to other suitable signals. In one or more embodiments, the shield region 36 can be electrically isolated.

Disposed on the redistribution layer 32 is the second passivation layer 38. In one or more embodiments, the second passivation layer 38 can be disposed on and in contact with one or more portions of the redistribution layer 32. In one or more embodiments, one or more additional layers can be disposed between the second passivation layer 38 and the redistribution layer 32. Further, in one or more embodiments, one or more portions of the second passivation layer 38 can be disposed between conductive traces 34 and shield regions 36 of the redistribution layer 32 such that these portions are disposed on the first passivation layer 30. Similarly, one or more portions of the first passivation layer 30 can be disposed between the conductive traces 34 and shield regions 36 of the redistribution layer 32 such that these portions are in contact with the second passivation layer 38. Although depicted as a single layer, the second passivation layer 38 can include any suitable number of sublayers.

The second passivation layer 38 can include any suitable material, e.g., the same material described herein regarding the first passivation layer 30. Further, the second passivation layer 38 can take any suitable shape and have any suitable dimensions.

Disposed on or at least partially within the second passivation layer 38 is the patterned conductive layer 40. Such patterned conductive layer 40 includes one or more conductive traces 42. Although shown as a single layer, the patterned conductive layer 40 can include any suitable number of sublayers. In one or more embodiments, one or more additional passivation layers can be disposed on and in contact with the patterned conductive layer 40 such that the patterned conductive layer is disposed between the additional passivation and the second passivation layer 38. The patterned conductive layer 40 can be configured to electrically connect the integrated circuit 22 to one or more additional devices or integrated circuits using any suitable technique. Further, the patterned conductive layer 40 can be disposed on the second passivation layer 38 using any suitable technique.

The patterned conductive layer 40 can include any suitable number of conductive traces 42. Such conductive traces 42 can take any suitable shape and have any suitable dimensions. In one or more embodiments, the patterned conductive layer 40 can include one or more conductive pads 43 that can be electrically connected to the redistribution layer 32 and the integrated circuit 22 using any suitable technique, e.g., utilizing one or more vias 48, 50.

Figure 5:
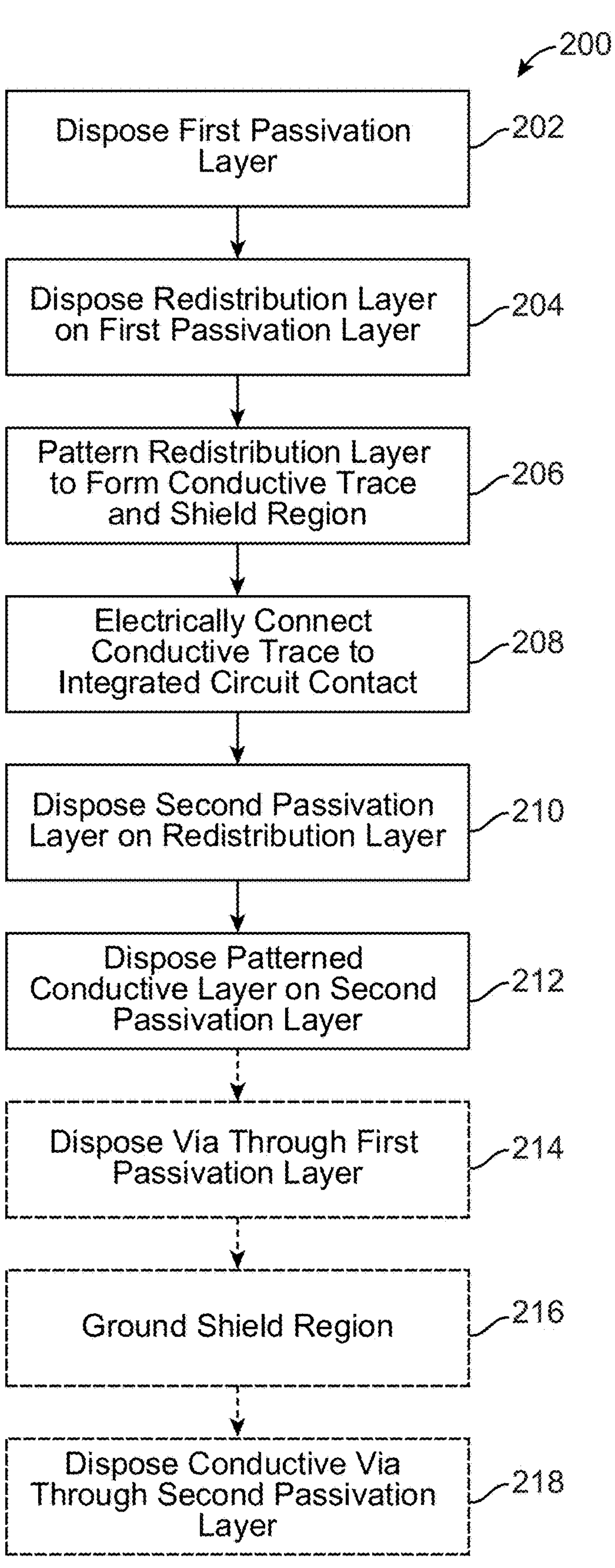
FIG. 5 is a flowchart of one method of forming the integrated circuit package of FIG. 1.

Any suitable technique can be utilized to form the integrated circuit package 20. For example, FIG. 5 is a flowchart of one embodiment of a method 200 of forming the integrated circuit package 20. Although described regarding the integrated circuit package 20 of FIGS. 1-3, the method 200 can be utilized to form any suitable integrated circuit package. At 202, the first passivation layer 30 can be disposed on the first major surface 24 of the integrated circuit 22 and the integrated circuit contacts 28 using any suitable technique. The redistribution layer 32 can be disposed on or at least partially within the first passivation layer 30 at 204 using any suitable technique. At 206, the redistribution layer 32 can be patterned using any suitable technique to form the conductive traces 34 and the shield regions 36. In one or more embodiments, a conductive layer or layers can be disposed on the first passivation layer 30 and patterned using any suitable technique to form the conductive traces 34 and shield regions 36. The conductive traces 34 of the redistribution layer 32 can be electrically connected to the integrated circuit contacts 28 using any suitable technique at 208. For example, one or more vias 48 can be disposed through the first passivation layer 30 at 214 that electrically connect the integrated circuit contacts 28 to the conductive traces 34.

At 210, the second passivation layer 38 can be disposed on the redistribution layer 32 using any suitable technique. In one or more embodiments, the second passivation layer 38 can be disposed such that one or more portions of such layer are disposed between one or more portions of the redistribution layer 32. The patterned conductive layer 40 can be disposed on or at least partially within the second passivation layer 38 at 212 using any suitable technique. For example, a conductive layer can be disposed on the second passivation layer 38, and such conductive layer can be patterned using any suitable technique to form the conductive traces 42 and conductive pads 43. In one or more embodiments, one or more vias 48 can optionally be disposed through the first passivation layer 30 at 214 using any suitable technique.

In one or more embodiments, the shield region 36 can optionally be grounded at 216 using any suitable technique. Further, at 218, one or more conductive vias can optionally be disposed through the second passivation layer 38 that electrically connect the redistribution layer 32 to the patterned conductive layer 40 using any suitable technique.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:

1. An integrated circuit package comprising:

an integrated circuit comprising a first major surface, a second major surface, and an integrated circuit contact disposed on the first major surface, wherein the integrated circuit contact provides one or more electrical connections between the integrated circuit and one or more devices external to the integrated circuit;

a first passivation layer disposed on the first major surface of the integrated circuit and over the integrated circuit contact;

a redistribution layer disposed on the first passivation layer, wherein the redistribution layer comprises a conductive trace and a shield region, wherein the conductive trace and the shield region define a plane of the redistribution layer;

a second passivation layer disposed on the redistribution layer; and a patterned conductive layer disposed on the second passivation layer and comprising a conductive trace, wherein a portion of the shield region of the redistribution layer is disposed between the conductive trace of the patterned conductive layer and the integrated circuit along an axis that is substantially orthogonal to the first major surface of the integrated circuit.

2. The integrated circuit package of claim 1, wherein the shield region of the redistribution layer is configured to reduce parasitic capacitance between the integrated circuit and the patterned conductive layer.

3. The integrated circuit package of claim 1, wherein the shield region of the redistribution layer is configured to dissipate ionizing radiation incident upon the shield region.

4. The integrated circuit package of claim 1, wherein the shield region of the redistribution layer comprises a mesh comprising a plurality of openings.

5. The integrated circuit package of claim 1, wherein the integrated circuit comprises a substrate and an active area disposed on the substrate, the active area comprising one or more electronic elements or devices of the integrated circuit, wherein the active area is electrically connected to the integrated circuit contact to provide electrical connection between the electronic elements or devices of the integrated circuit and one or more devices that are external to the integrated circuit.

6. The integrated circuit package of claim 5, wherein the integrated circuit contact is electrically connected to the redistribution layer by a conductive via that extends through the first passivation layer.

7. The integrated circuit package of claim 1, wherein the shield region is grounded.

8. The integrated circuit package of claim 1, wherein the patterned conductive layer further comprises a conductive pad electrically connected to the redistribution layer and the integrated circuit.

9. A medical device comprising a housing and circuitry disposed within the housing, wherein the circuitry comprises an integrated circuit package comprising:

an integrated circuit comprising a first major surface, a second major surface, and an integrated circuit contact disposed on the first major surface;

a first passivation layer separate from the integrated circuit and disposed on the first major surface of the integrated circuit and over the integrated circuit contact;

a redistribution layer disposed on the first passivation layer, wherein the redistribution layer comprises a conductive trace and a shield region, wherein the conductive trace and the shield region define a plane of the redistribution layer;

a second passivation layer disposed on the redistribution layer; and a patterned conductive layer disposed on the second passivation layer and comprising a conductive trace, wherein a portion of the shield region of the redistribution layer is disposed between the conductive trace of the patterned conductive layer and the integrated circuit along an axis that is substantially orthogonal to the first major surface of the integrated circuit.

10. The medical device of claim 9, wherein the shield region of the redistribution layer is grounded to the housing.

11. The medical device of claim 9, further comprising an electrode disposed on an outer surface of the housing, wherein the integrated circuit package is electrically connected to the electrode.

12. The medical device of claim 9, wherein the shield region of the redistribution layer is configured to reduce parasitic capacitance between the integrated circuit and the patterned conductive layer.

13. The medical device of claim 9, wherein the shield region of the redistribution layer comprises a mesh comprising a plurality of openings disposed through the shield region.

14. The medical device of claim 9, wherein the integrated circuit comprises a substrate and an active area disposed on the substrate, the active area including one or more electronic elements or devices of the integrated circuit, wherein the active area is electrically connected to the integrated circuit contact to provide electrical connection between the electronic elements or devices of the integrated circuit and one or more devices that are external to the integrated circuit.

15. An integrated circuit package that incorporates an integrated circuit with a plurality of layers, wherein the integrated circuit comprises a first major surface, a second major surface, and an integrated circuit contact disposed on the first major surface, and further wherein the plurality of layers comprises:

a first passivation layer disposed on the first major surface of the integrated circuit and over the integrated circuit contact;

a redistribution layer disposed on the first passivation layer, wherein the redistribution layer comprises a conductive trace and a shield region, wherein the conductive trace and the shield region define a plane of the redistribution layer;

a second passivation layer disposed on the redistribution layer; and a patterned conductive layer disposed on the second passivation layer and comprising a conductive trace, wherein a portion of the shield region of the redistribution layer is disposed between the conductive trace of the patterned conductive layer and the integrated circuit along an axis that is substantially orthogonal to the first major surface of the integrated circuit.

16. The integrated circuit package of claim 15, wherein the integrated circuit contact provides electrical connection between the integrated circuit and one or more devices external to the integrated circuit.

17. The integrated circuit package of claim 15, wherein the shield region of the redistribution layer comprises a mesh comprising a plurality of openings.

18. The integrated circuit package of claim 15, wherein the integrated circuit comprises a substrate and an active area disposed on the substrate, the active area comprising one or more electronic elements or devices of the integrated circuit, wherein the active area is electrically connected to the integrated circuit contact to provide electrical connection between the electronic elements or devices of the integrated circuit and one or more devices that are external to the integrated circuit.

19. The integrated circuit package of claim 18, wherein the integrated circuit contact is electrically connected to the redistribution layer by a conductive via that extends through the first passivation layer.

20. The integrated circuit package of claim 15, wherein the shield region is grounded.

* * * * *